United States Patent [19]

Field et al.

[11] Patent Number: 4,663,621

[45] Date of Patent: May 5, 1987

[54] MEDICINE CABINET

[76] Inventors: David J. Field, 5 Station Road, Rosslare County Wexford, Strand, Rosslare; James F. X. Stafford, Arran Cottage, Crossabeg, County Wexford, both of Ireland

[21] Appl. No.: 595,882

[22] Filed: Apr. 2, 1984

[51] Int. Cl.⁴ .................. G06F 7/04; E05B 45/06; A47F 1/04
[52] U.S. Cl. .................. 340/825.31; 340/542; 340/365 R; 340/825.32; 221/154; 221/2; 128/666; 312/209
[58] Field of Search .................. 340/825.31, 825.32, 340/825.56, 541, 543, 545, 628, 365 R, 331, 309.4; 368/246; 312/209; 128/666, 667, 706; 200/61.62, 61.64; 221/2, 154

[56] References Cited

U.S. PATENT DOCUMENTS

| | | | |
|---|---|---|---|
| 3,762,601 | 10/1973 | McLaughlin | 221/2 |
| 3,988,909 | 11/1976 | Catapano | 312/209 |
| 3,998,356 | 12/1976 | Christensen . | |
| 4,118,700 | 10/1978 | Lenihan | 340/545 |
| 4,121,574 | 10/1978 | Lester | 128/666 |
| 4,142,097 | 2/1979 | Ulch | 340/825.31 |
| 4,148,092 | 4/1979 | Martin . | |
| 4,275,384 | 6/1981 | Hicks et al. | 221/2 |
| 4,404,550 | 9/1983 | Shaw | 340/628 |
| 4,439,647 | 3/1984 | Calandrello et al. | 340/365 R |
| 4,490,711 | 12/1984 | Johnston | 368/246 |
| 4,495,540 | 1/1985 | Remington et al. | 340/825.31 |
| 4,534,056 | 8/1985 | Feilchenfeld et al. | 340/825.31 |

OTHER PUBLICATIONS

Gunnar Gotschalken, electronic Design, "Build a Warbling Alarm Generator With Two Op-Amp Oscillators," vol. 25, Mar. 29, 1977, p. 108.

*Primary Examiner*—Ulysses Weldon
*Assistant Examiner*—Ralph E. Smith
*Attorney, Agent, or Firm*—Townsend and Townsend

[57] ABSTRACT

A medicien cabinet has a housing and a door. The door is provided with an electrically operated lock which is operable by using the push keys. The opening code for the lock is initially set by inserting four keys into four holes in a four by ten array of holes provided in the casing on the inside of the door. The circuits for the code pre-setting and code inputting circuits are provided on a membrane.

The cabinet is provided with a light emitting diode (LED) and a buzzer which can be operated by timing means at set intervals. The LED and the buzzer also operate while the door is open.

Additional facilities may also be provided on the cabinet.

7 Claims, 12 Drawing Figures

MEDICINE CABINET

FIELD OF THE INVENTION

The invention relates to cabinets and particularly to cabinets for housing medicines.

SUMMARY OF THE INVENTION

The present invention provides a medicine cabinet comprising an electrically operated combination lock which is operable on inputting a combination code equivalent to a pre-set code, means for setting the pre-set code, means for inputting a code, means for comparing the inputted code with the pre-set code and means for opening the lock when the inputted code is equivalent to the pre-set code, signal emitting means, and timing means for operating the signal emitting means so as to produce a reminer signal to remind a user to take or administer medication.

Advantageously, means are provided for operating the signal emitting means so as to produce an alarm signal while the cabinet is open and the lock comprises a solenoid having a spring loaded piston which is engageable with a keeper on de-energisation of the solenoid.

Preferably, the means for setting the pre-set code and the means for inputting a combination to open the lock comprises a single membrane having two portions, a code setting portion and a code inputting portion, each membrane portion having two layers with a conductive circuit on each layer, a spacing element having a plurality of holes between the two layers, and means for applying pressure to discrete regions of the membrane, so as to form electrical connections between the layers of the membrane through the holes of the spacing element.

The membrane may be mounted in a casing one face of which is provided with a plurality of holes, each of which is adapted to accommodate a key which may be used to make an electrical connection between the layers of the membrane of the code setting portion, and with a second face of the casing having a plurality of push buttons which may be used to make electrical connections between the layers of the membrane of the code inputting portion.

Conveniently, the means for comparing the inputted code with the pre-set code comprises an integrated circuit element, means for translating the electrical outputs from the code setting means and the code inputting means to provide the integrated circuit element with the required electrical inputs, electrical logic means for producing an incorrect code detection signal whereby the integrated circuit element using said signal and the electrical outputs of the code inputting means is able to detect the selection of a correct code and the timing means comprises an integrated circuit timing element operable to produce an electrical output once every set time period and means for adjusting said time period.

Preferably, the signal emitting means comprises electrical logic means, frequency oscillating means and signal producing means, the electrical logic means accepting electrical inputs from the electronic circuitry to produce an electrical output which is transmitted to the frequency oscillating means which in turn activates the signal producing means and the frequency oscillating means includes a first oscillator and a second oscillator and the signal producing means comprises a visual indicator and an audible indicator, the visual indicator being operable by the first oscillator and the audible indicator being operable by the second oscillator.

BRIEF DESCRIPTION OF THE DRAWINGS

The invention will now be described more particularly, by way of example, with reference to the accompanying drawings, in which.

DESCRIPTION OF THE PREFERRED EMBODIMENTS

Figure 1:
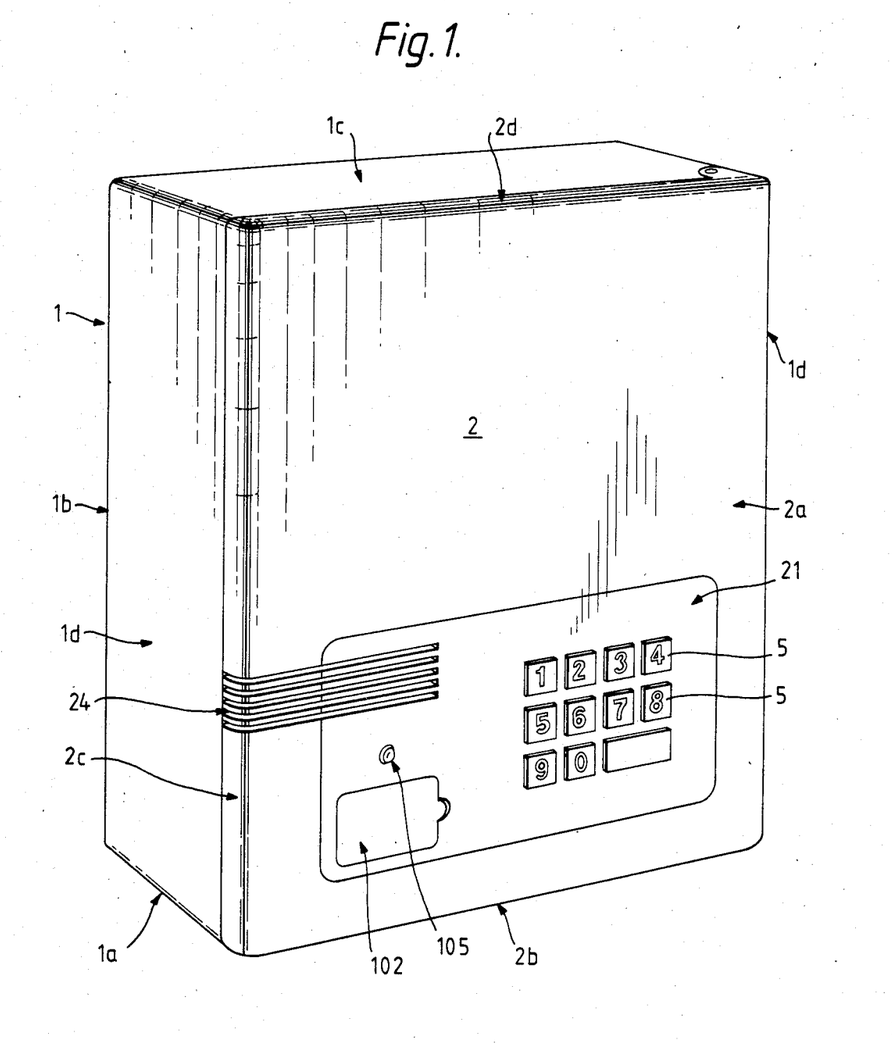
FIG. 1 is a perspective view of a cabinet according to the invention.
Figure 2:
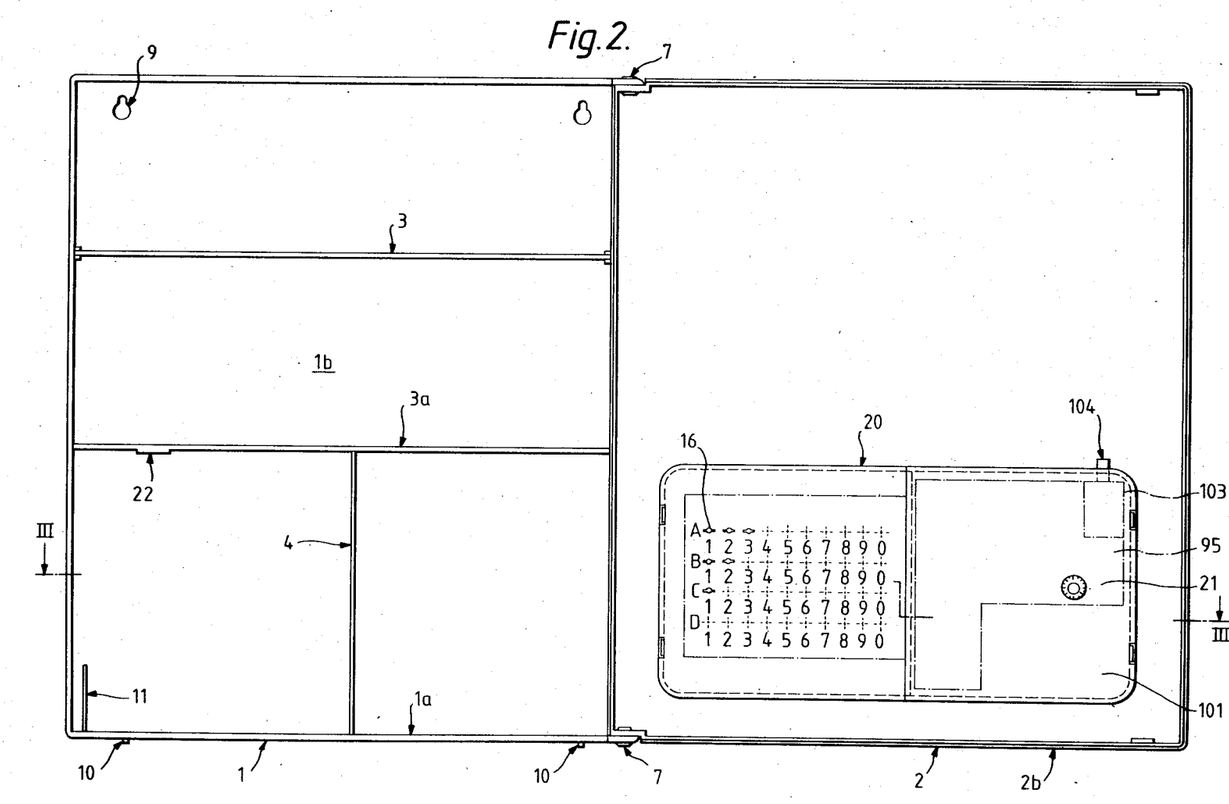
FIG. 2 is a front elevation of the cabinet of FIG. 1, with the door opened through one hundred and eighty degrees.
Figure 3:
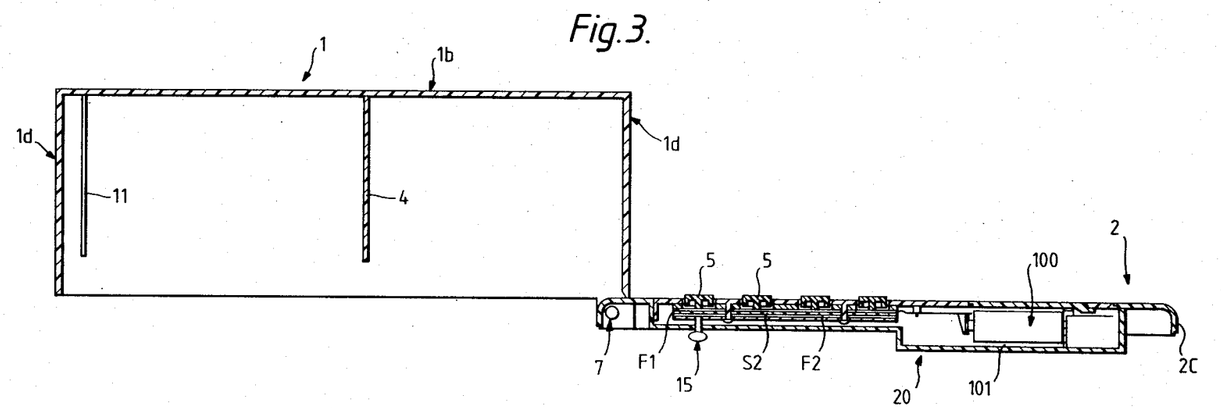
FIG. 3 is a sectional plan view on line III—III of FIG. 2.

Referring to the drawings and initially to FIGS. 1, 2 and 3, the cabinet comprises a moulded housing 1 having a bottom panel 1a, rear panel 1b, top panel 1c and two side panels 1d, the housing 1 having hinged thereto a moulded door 2 comprising a front panel 2a with rearwardly extending bottom, top and side lips 2b, 2c and 2d. In the closed position of the door 2, as seen in FIG. 1, the lips 2b, 2c and 2d engage end to end with the front edges of the bottom, top and side panels 1a, 1c and 1d of the housing 1. The cabinet is manufactured from an acrilonitrile-butadiene-styrene (ABS) copolymer.

The cabinet has a four digit coded combination lock operable by push keys 5, i.e. to open the cabinet the four digits of the code must be sequentially keyed in using the push keys 5. The code of the combination lock may be reset by the user. The lock and its details of operation will be described in more detail hereinafter.

Figure 4:
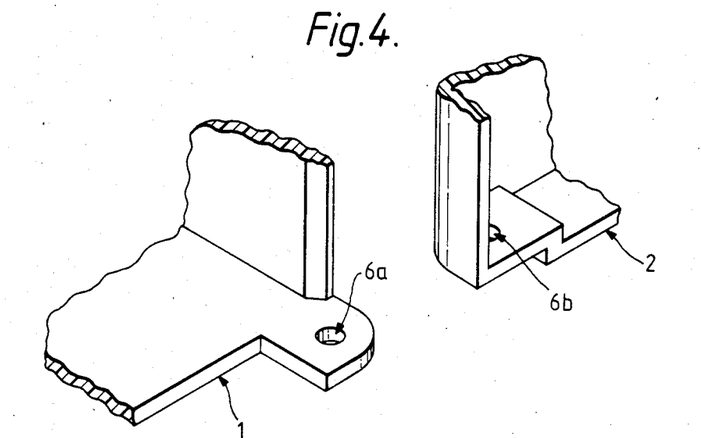
FIG. 4 is a perspective fragmentary exploded view of the hinge arrangement of the cabinet.

The door 2 is hinged to the housing 1 by hinge rivets 7 which pass through corresponding holes 6a, 6b provided in the cabinet housing 1 and door 2 (see FIGS. 2 and 4). The cabinet housing 1 has shelves 3 and 3a, and a vertical partition 4 between shelf 3a and bottom panel 1a. The cabinet may be mounted on a wall, for which purpose screw receiving holes 9 are provided in the rear panel 1b. Alternatively, the cabinet may be freestanding, for which purpose supports 10 are provided which keep the bottom panel 1a of the housing and the bottom lip 2b of the door 2 clear of the surface on which the cabinet stands.

The cabinet is provided with a desiccant (not shown) to control the humidity. As may be seen in FIG. 2, a compartment wall 11 is provided at the bottom left hand side of the cabinet housing 1, to receive and locate the desiccant.

The cabinet is intended primarily for use in the storage of medicines in the home and for preventing young children from getting access to the medicines. As a safety feature the four digit combination code may be reset if it is feared that a child might become familiar with a particular combination code. Because the cabinet is manufactured from a plastics material, the cabinet may, in the event of an emergency, be forced open, for example, by prying open the door with a screwdriver.

Figure 5:
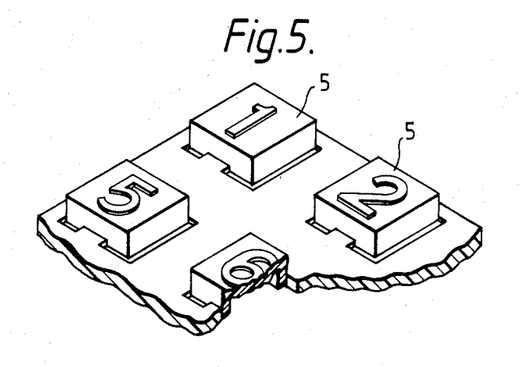
FIG. 5 is a perspective view of a portion of the keyboard of the cabinet.

The push keys 5 (see FIG. 5) are extra large to facilitate handicapped or arthritic patients. The numerals of the keys 5 are raised and colour printed to assist the blind or partially blind.

The cabinet is provided with electronic circuitry for operating the combination lock and for producing reminder and alarm signals. The electronic circuitry is mounted in a generally rectangular casing 20 provided in the cabinet door. A front cover 21 flush with the front face of the door 2 protects the circuitry.

The electronic circuitry is powered by a battery 100 (see FIG. 3) which is located in a compartment 101 within the casing 20, and accessible from outside the cabinet through a hatch 102 in the front cover 21. The electronic circuitry may also of course be operated from mains electricity.

The locking mechanism includes a solenoid 103 mounted at one corner of the casing 20. When the lock is operated piston 104 of the solenoid 103 engages a keeper 22 formed in the shelf 3a.

Incorporated into the electronic circuitry is a time delay feature. If a user of the cabinet keys in an incorrect four digit combination, then the electronic circuity shuts down for a predetermined time interval, for example ten seconds, before the circuitry will accept a further four digit combination. Such a feature prevents a person from quickly keying in random four digit combinations into the circuitry in an attempt to find the correct code.

Referring to FIG. 1, the reminder and alarm signals are produced by both a light emitting diode (LED) 105 and a piezo electric buzzer (not shown in FIG. 1) located behind grille 24 in the front cover 21. The LED 105 produces a flashing light and the buzzer produces a buzzing sound under a number of conditions.

Reminder signals are emitted to remind a patient of a medication dosage interval. For this purpose, the circuitry includes a timer-circuit on which the dosage interval may be set.

Alarm signals are produced when the door 2 is opened, thus giving a warning that the cabinet is open. To turn off the alarm signals it is necessary to close the door 2 of the cabinet.

A signal in the form of a short bleep from the buzzer is produced whenever a push key is pressed, except when the key is pressed immediately after a dosage interval reminder, thus indicating that someone is opening or attempting to open the cabinet.

The LED 105 also comes on whenever the battery runs low.

Two embodiments of electronic circuit will now be described, the first embodiment being described with reference to FIGS. 1 to 11 and the second embodiment being described with reference to FIG. 12.

Figure 6:
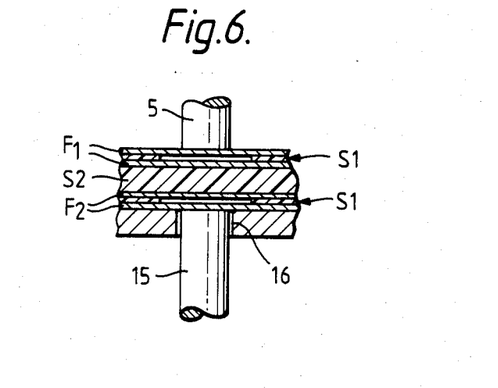
FIG. 6 is a sectional view of a portion of the combination code setting and selection mechanism of the cabinet.
Figure 7:
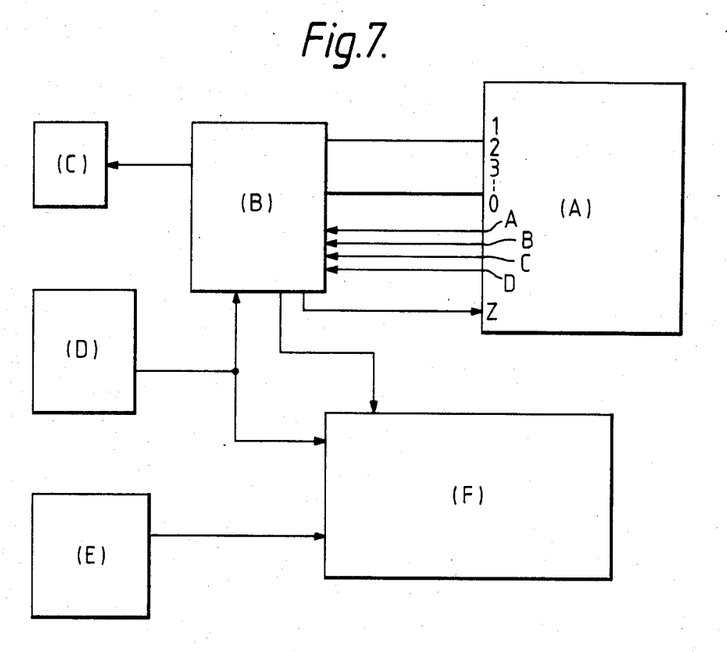
FIG. 7 is a block diagram of a first embodiment of electronic circuitry for the cabinet.

FIG. 7 is a block diagram of the first embodiment which consists of the following:
(A)—code pre-setting and code inputting circuit
(B)—code detector circuit
(C)—door lock mechanism
(D)—door status detector
(E)—timer circuit
(F)—signal emitting circuit The code pre-setting and code inputting circuit (A) will now be described in more detail. The circuit (A) employs membrane switch technology, and consists of a single membrane housed within the casing 20 of the cabinet door 2. The conductive circuit printed on the membrane is shown in FIG. 10. Lines A to D, 0 to 9 and Z at the top left hand corner of FIG. 10 form an edge connector for connection to the printed circuit board 95 (see FIGS. 2 and 9). Two fold lines are shown on the membrane. That part F1 of the membrane to the right of fold line II—II is the code pre-setting circuit and that part F2 of the membrane to the left of the fold line II—II is a membrane switch code inputting circuit (i.e. key pad). The membrane is first folded along line I—I so that lines A, B, C and D overlap lines 0 to 9 and lines Z1, Z2 and Z3 overlap the thickened vertical sections of lines 0 to 9. An insulating spacer S1 (see FIG. 6) is inserted between the overlapping circuits. An insulating spacer S1 (see FIG. 6) having a plurality of holes corresponding to the cross over points of the conductors is placed between the upper and lower membranes. Thus pressing the upper and lower membranes together at these cross over points will result in electrical contact between associated upper and lower conductors. The printed membrane and insulating spacer membrane are then folded along line II—II so that the two layers of circuit F1 overlap the two layers of circuit F2, and an insulating pad S2 is inserted between F1 and F2. The arrangement of the layers is best seen in FIG. 6. The four digit combination code is pre-set by bringing conductive lines on the two layers of circuit F1 into contact with one another. The contact is made by four keys 15 pushing the two layers into contact with one another through four holes in membrane S1, the four holes being chosen from a 4×10 array of holes (one code pre-setting key and hole are shown in FIG. 6).

Figure 11:
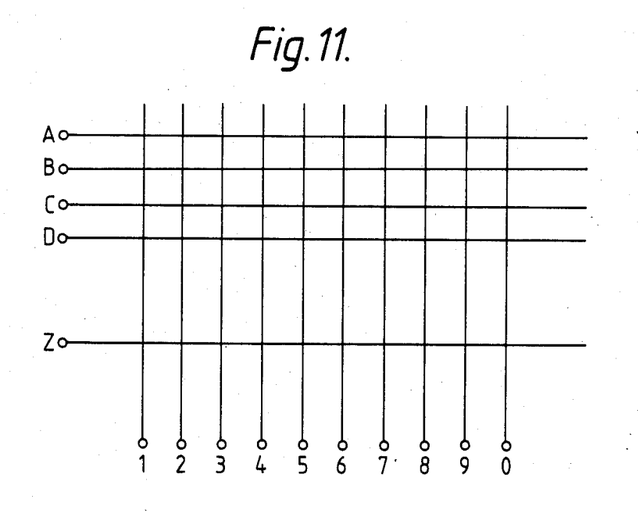
FIG. 11 is a schematic view of the conductive ink circuit of the code selection mechanism.
Figure 12:
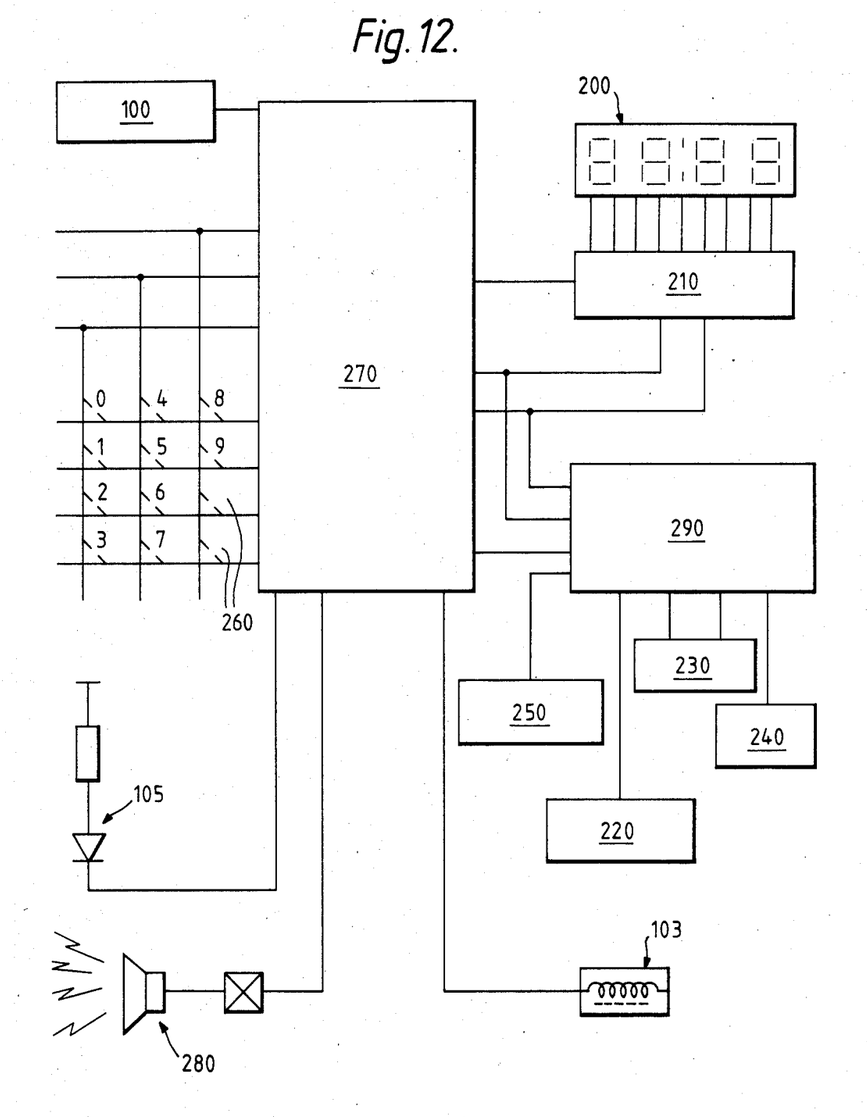
FIG. 12 is a block diagram of a second embodiment of electronic circuitry.

The schematic for the circuit (A) is shown in FIG. 11. Voltage is supplied to the circuit by line Z. The combination code for the cabinet is pre-set by first bringing each of the four horizontal lines A, B, C and D into contact with one of the ten vertical lines 0 to 9. When a code is inputted into the circuit, the line Z is brought into contact with one of the ten vertical lines thus sending a signal along the vertical line. Should that vertical line be associated with one of the four horizontal lines A to D, then a signal will also be sent along the associated horizontal line.

The signals on lines A to D are transmitted to pins 11, 12, 13, 14 of the integrated circuit U2. To re-set the code, the keys are moved to different holes in the 4×10 array. In a similar manner, the push keys 5 bring the conductors on the thickened vertical sections of lines 0 to 9 into contact with conductors Z1, Z2 and Z3 on the two layers of circuit F2 into contact with one another, thereby sending signals to pin 10 of U2. The pre-set code and the inputted code are compared by U2.

To the user of the cabinet, the keys 15 for setting the code are each inserted in a separate hole 16 in a different row of a 4×10 array of holes 16 in the casing 20 (see FIG. 2). Alternatively, the four keys may each be slidable on a separate rail to any one of ten positions.

Referring again to FIG. 7, (B) to (F) are all mounted on an L-shaped printed circuit board 95, the outline of which is shown in FIG. 2. The layout of the printed circuit board 95 is shown in FIG. 9.

Figure 8:
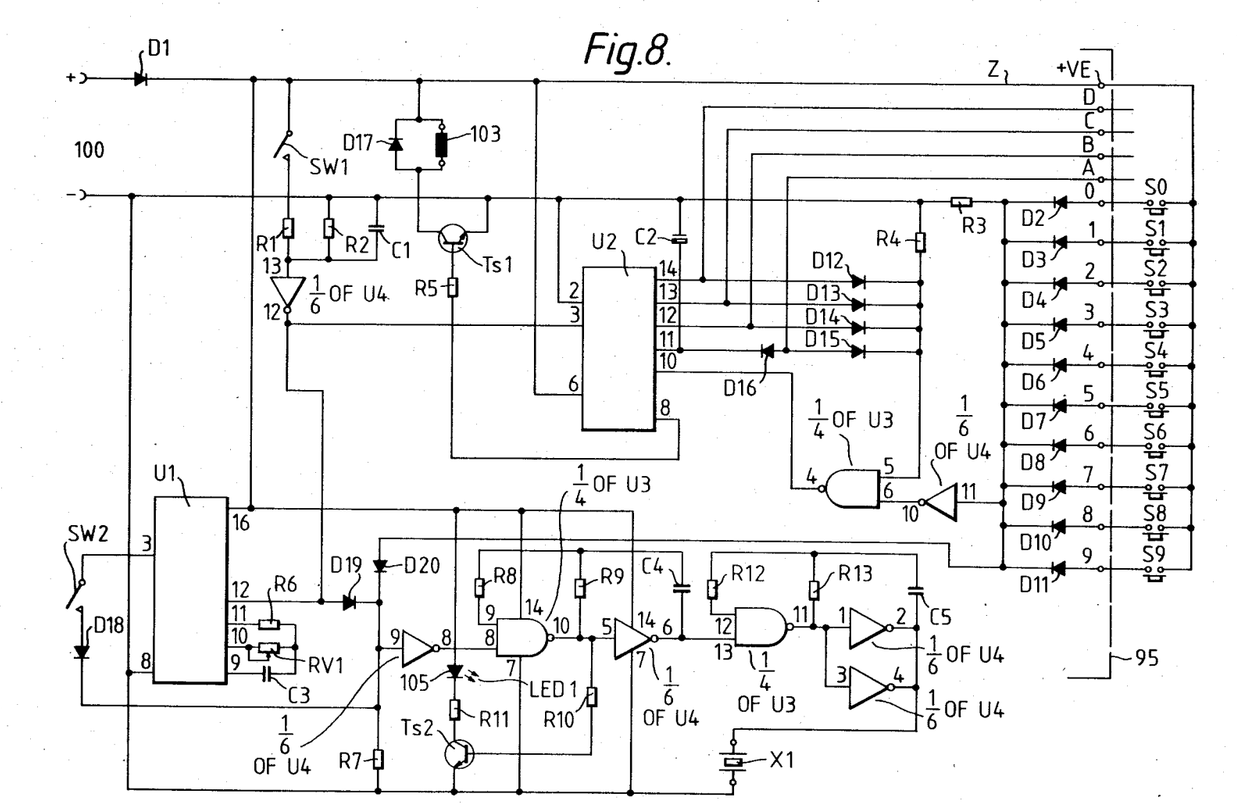
FIG. 8 is a circuit diagram of the electronic circuitry of FIG. 7.
Figure 9:
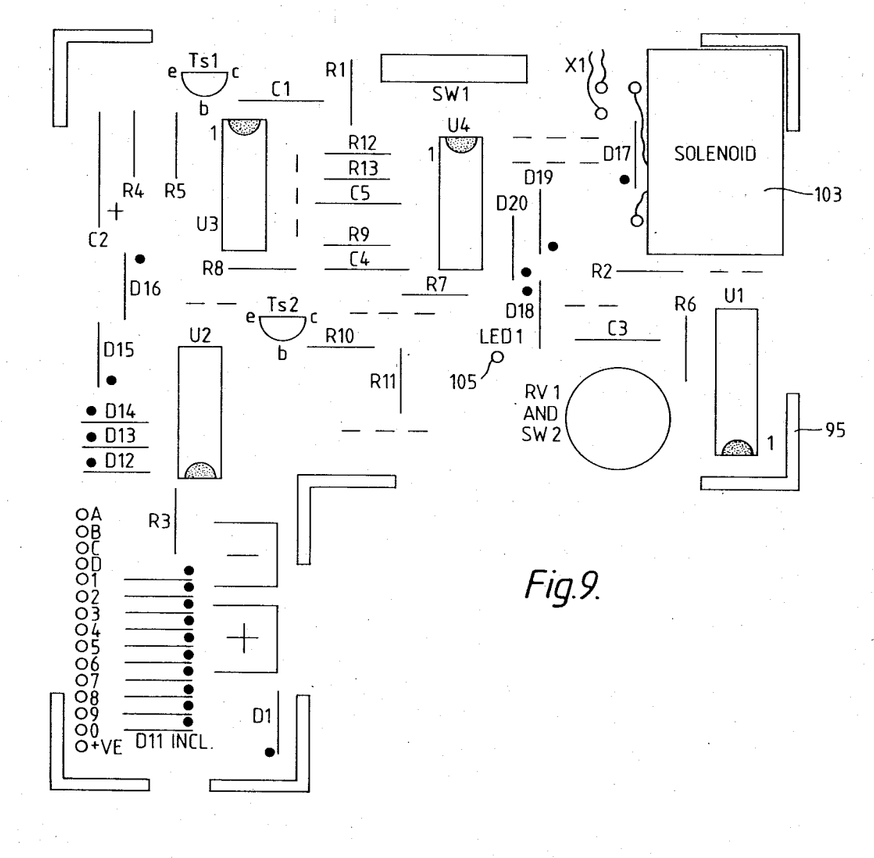
FIG. 9 is a plan view of a marked out printed circuit board for receiving the components of the circuit shown in FIG. 8.
Figure 10:
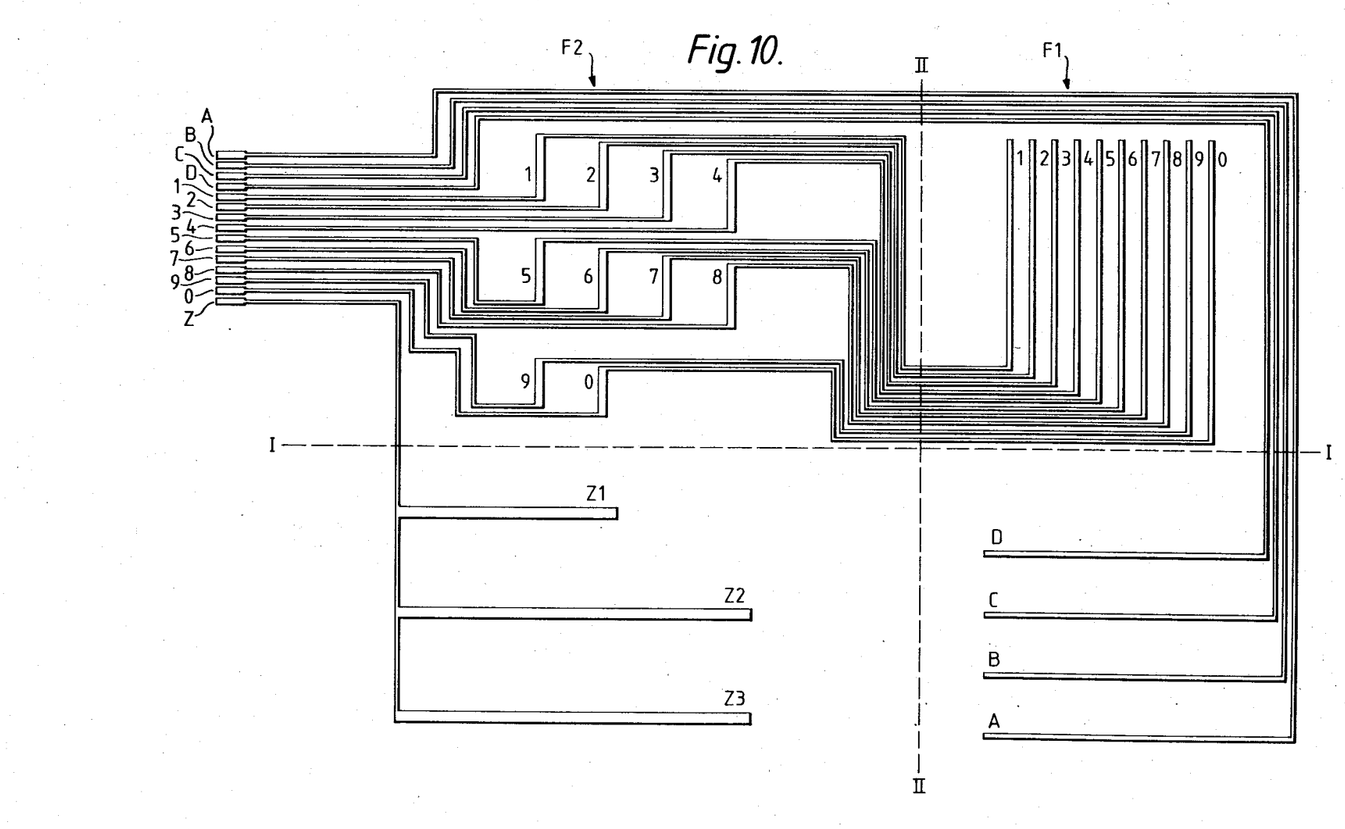
FIG. 10 is a plan view of a membrane having a conductive ink circuit, the membrane forming part of the combination code setting and selection mechanism.

Referring to FIGS. 7, 8 and 9, the code detector circuit (B) comprises a large scale integrated circuit U2 (LS1 7225) and associated passive components which translate the outputs from the code setting and selecting mechanism to provide U2 with the required inputs. Of these passive components diodes D2 to D11 form a key detector which informs U2 that a push key 5 has been depressed and diodes D12 to D15 perform a similar function for the four code digits which have been set by the keys 15. These diodes in association with an exclusive —OR logic gate formed by logic gates of the NOR and INVERTER integrated circuits perform an incorrect code detector input. With this input and the inputs from the push keys 5 the integrated circuit U2 is able to detect a correct code sequence.

The door opening and locking circuit (C) consists of the solenoid 103 operated from the code detector circuit (B) by means of a drive transistor Ts1, so as to withdraw the piston 104 when the correct digit combination code is detected to allow the door 2 to be opened. When the door 2 is opened the piston 104 is released. To facilitate closing of the door 2 the piston 104 is spring loaded.

The door status detector circuit (D) comprises a switch SW1 and associated resistors and capacitors. Its function is to reset all electronic functions when the cabinet door 2 is closed and provide an input to the signal emitting circuit (F) when the door is open.

Switch SW1 is a contact switch (not shown in Figure 2) which is mounted on the casing 20 of the cabinet door 2 and is closed when the cabinet door is closed. Movement of the door 2 a distance beyond 2 mm opens SW1 to operate the alarm circuit (F) and release the solenoid 103. Reclosing the door 2 closes switch SW1 which resets all the electronic functions including the timer circuit (E).

The timer circuit (E) comprises an integrated circuit U1 (4060) and associated resistors and capacitors. The timer circuit operates continuously but is only allowed to trigger the alarm when switch SW2 is closed. The basic clock frequency is a half a second which is divided by fourteen binary stages to give an alarm output every 86,400 seconds (24 hours). This time interval can be reduced to a minimum of 900 seconds (15 minutes) by adjustment of potentiometer RV1. To the user the potentiometer is in the form of a manually operable rotary dial 21 mounted on the casing 20. Switch SW2 is closed by pushing dial 21 inwardly towards the casing.

The signal emitting circuit (F) consists of a logic OR input, a low frequency oscillator, a high frequency oscillator, a visual signal emitter or LED 105 and an audible signal emitter or buzzer.

The logic OR function comprises diodes D18, D19 and D20 which accept inputs from the timer, the door status and the keyboard circuits and provide a logic 1 output to the low frequency oscillator when any combination of these inputs are at logic 1.

A logic 1 output from the above logic OR activates the signal emitter as follows:

The first oscillator comprises an inverter gate from the INVERTER integrated circuit U3, a NOR gate from the NOR integrated circuit U4, and associated resistors and capacitors to control the frequency of oscillation. The passive components are designed for an oscillation frequency of 5 Hertz.

The second oscillator is identical but has a dual inverter output stage to drive the audible alarm X1. The passive components for this stage are designed for an oscillation frequency of 4,500 Hertz.

The visual signal emitter comprises a drive transistor and associated light emitting diode (LED1) 105 which is driven from the first oscillator.

The audible signal emitter consists of a piezo electric resonator X1 which is driven from the second oscillator which in turn is activated by the first oscillator.

The second embodiment of electronic circuitry will be described with reference to FIG. 12. The circuitry of the first embodiment is replaced by a single customized mask-programmed 4-bit CMOS microprocessor chip 270 which contains the necessary RAM and ROM components for the operation of the cabinet.

The second embodiment also includes additional features such as a 4.5 digit liquid crystal display 200 controlled by a controller 210; a thermometer 220; a heart rate monitor 230; a smoke sensor 240 and a voice recognition chip 250.

The keypad has two additional functional keys 260, which control such functions as clock and alarm time settings, alarm muting, thermometer, and heart rate monitor.

The microprocessor chip 270 contains counter/timer hardware and a master oscillator. The microprocessor software uses this hardware to provide a real time programmable clock and associated programmable alarm times.

When the real time coincides with the alarm time the software then jumps to a routine which activates the visual and audible signal emitters which are driven directly from the microprocessor.

The 4.5 digit LCD display 200 may be driven, either via the LCD controller I.C. 210 or directly by the microprocessor 270 and can display not only time but also heart rate and temperature when required. The display flashes on and off when the microprocessor detects that the battery voltage is low.

The audible signal comprises a piezo buzzer 280 resonant at 4,500 Hertz. The microprocessor outputs drive the buzzer directly. The visual signal emitter again comprises a light emitting diode (LED) 105 and associated resistor. The LED is driven directly at a frequency of 5 Hertz.

The thermometer 220 comprises a temperature sensitive transducer (temperature to voltage converter) and an analog to digital converter 290 which converts the voltage into usable digital information. The microprocessor 270 reads this data, converts it into usable temperature data using an algorithm and displays the resulting temperature on the LCD display 200.

The heart rate monitor 230 uses an infrared detector to measure the pulse rate of the patient. The detector is placed on a person's wrist. As the blood pulses through the wrist the intensity of the detected heat changes. Thus the microprocessor which receives this information via the analog to digital converter 290 can compute the heart rate and subsequently display it on the LCD display 200.

The smoke sensor 240 when activated by the presence of smoke causes the alarm circuit to emit signals.

The voice recognition chip 250 enables a severely handicapped person to speak the four digit combination code and thereby open the cabinet.

We claim:

1. A medicine cabinet comprising:
   a housing having an internal cavity for storing medicine accessible through an opening in said housing;
   access means for gaining access to the interior of said housing, the access means including a door sized to cover said opening when placed in a closed position and lock means for releasably securing said door in said closed position;
   said lock means including means for inputting a code and means responsive to entry of predetermined combination code for releasing said lock means;
   reminder signal means for issuing an audible reminder signal at periodic intervals set by a user;
   access alarm means for issuing an audible access alarm in response to an operation of said access means, the access alarm means including means responsive to operation of said inputting means for issuing said access alarm; and
   means for inhibiting said access alarm means after issuance of said reminder signal.

2. A medicine cabinet according to claim 1 and further including
   an externally accessible compartment on one of said housing and door for receiving a battery;
   wherein the lock means includes
      an electrically operable latch for releasing said door in response to an electrical door release signal and for securing said door in said closed position when no electrical signal is applied; and
      means, adapted to be powered by said battery, for issuing said door release signal to said latch in response to predetermined user input.

3. A medicine cabinet according to claim 2, wherein said lock means includes a keyboard having a plurality of user operable keys, said predetermined user input comprises entry of a predetermined combination code on said keyboard, and said issuing means includes delay means responsive to key entry of a code other than said combination code for inhibiting said door release signal for a predetermined time period.

4. A medicine cabinet according to claim 1, further comprising:
   switch means for sensing when said door is in said closed position, and
   means responsive to said switch means for setting said lock means when said door is moved to said closed positon and for issuing an audible door open alarm when said door is opened.

5. A medicine cabinet according to claim 4 further comprising:
   a temperature sensitive transducer responsive to the body temperature of a human subject for emitting an electrical signal corresponding to the subject's body temperature;
   a light sensitive transducer responsive to the light intensity of the blood of a human subject for emitting an electrical signal corresponding to the subject's pulse rate;
   a smoke sensitive transducer responsive to smoke for emitting an electrical signal corresponding to the amount of smoke in the environment of said medicine cabinet; and
   a control device mounted to one of said housing and door and electrically coupled to said temperature transducer, light transducer and smoke transducer, including:
   means responsive to said temperature electrical signal for displaying the body temperature of said subject;
   means responsive to said pulse electrical signal for displaying the pulse rate of said subject; and
   means responsive to said smoke electrical signal for issuing an audible smoke alarm.

6. A medicine cabinet according to claim 1, wherein said housing and door are cooperatively constructed of a user deformable material to permit said door to be forced open without releasing said lock means, in the event of an emergency.

7. A medicine cabinet comprising:
   a housing having an opening for gaining access to medicine therein;
   a door associated with said housing and sized to cover said opening when placed in a closed position;
   lock means for releasably securing said door in said closed position, including:
   means for setting a predetermined combination code;
   means for inputting a code;
   means for comparing a code entered on said inputting means with said predetermined code;
   means responsive to said comparing means for releasing said door when said entered code is equivalent to said predetermined code;
   said lock means including a single membrane mounted so as to provide two opposed portions respectively facing the exterior and interior of said cabinet, said exterior facing portion comprising said code inputting means and said interior facing portion comprising said code setting means;
   each said membrane portion including two opposed layers of said single membrane with a conductive circuit on each layer, a spacing element having a plurality of holes positoined between said two layers, and means for applying pressure to discrete regions of said membrane, so as to form electrical connections between said layers of said membrane through the holes of said spacing element.

* * * * *